United States Patent
Shinkawa et al.

(10) Patent No.: US 10,266,833 B2
(45) Date of Patent: *Apr. 23, 2019

(54) NUCLEIC ACID SEQUENCE FOR PROTEIN EXPRESSION

(71) Applicant: HONDA MOTOR CO., LTD., Minato-Ku, Tokyo (JP)

(72) Inventors: Satoru Shinkawa, Saitama (JP); Shigenobu Mitsuzawa, Saitama (JP); Maiko Tanaka, Saitama (JP); Masayuki Machida, Hokkaido (JP); Hiroko Hagiwara, Ibaraki (JP); Hideaki Koike, Ibaraki (JP); Mahoko Kuninaga, Ibaraki (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/745,070

(22) PCT Filed: Jul. 15, 2016

(86) PCT No.: PCT/JP2016/003361
§ 371 (c)(1),
(2) Date: Jan. 15, 2018

(87) PCT Pub. No.: WO2017/010109
PCT Pub. Date: Jan. 19, 2017

(65) Prior Publication Data
US 2018/0201942 A1    Jul. 19, 2018

(30) Foreign Application Priority Data
Jul. 16, 2015    (JP) .................................. 2015-142213

(51) Int. Cl.
*C12N 15/80* (2006.01)
*C07K 14/38* (2006.01)
*C12N 9/24* (2006.01)
*C12N 15/63* (2006.01)

(52) U.S. Cl.
CPC .............. *C12N 15/80* (2013.01); *C07K 14/38* (2013.01); *C12N 9/2402* (2013.01); *C12N 15/63* (2013.01); *C12Y 302/01031* (2013.01)

(58) Field of Classification Search
None
See application file for complete search history.

(56) References Cited

U.S. PATENT DOCUMENTS

| 9,567,563 B2 * | 2/2017 | Shinkawa | C07K 14/38 |
| 2013/0196374 A1 | 8/2013 | Koishihara | |
| 2016/0230140 A1 * | 8/2016 | Shinkawa | C07K 14/38 |

FOREIGN PATENT DOCUMENTS

| EP | 0 238 023 A2 | 9/1987 |
| JP | 3343567 B2 | 11/2002 |
| JP | 2012-075369 A | 4/2012 |
| WO | 98/01470 A1 | 1/1998 |

OTHER PUBLICATIONS

Accession JU444216. Aug. 8, 2012. (Year: 2012).*
Marui et al., "Kojic acid biosynthesis in Aspergillus oryzae is regulated by a Zn (II) (2) Cys (6) transcriptional activator and induced by kojic acid at the transcriptional level", Journal of Bioscience and Bioengineering, Jul. 2011, vol. 112, No. 1, pp. 40-43.
Tsuboi et al., "Improvement of the Aspergillus oryzae Enolase Promoter (P-enoA) by the Introduction of cis-Element Repeats", Bioscience, Biotechnology, and Biochemistry, Jan. 2005, vol. 69, No. 1, pp. 206-208.
Gomi et al., "Molecular Cloning and Characterization of a Transcriptional Activator Gene, amyR, Involved in the Amylolytic Gene Expression in Aspergillus oryzae", Bioscience Biotechnology Biochemistry, Japan Society for Bioscience, Biotechnology, and Agrochemistry, Tokyo, Japan, Apr. 1, 2000, vol. 64, No. 4, pp. 816-827.
MacPherson et al., "A Fungal Family of Transcriptional Regulators: the Zinc Cluster Proteins", Microbiology and Molecular Biology Reviews: MMBR Sep. 2006, vol. 70, No. 3, pp. 583-604.
Tsukagoshi et al., "Regulation of the amylolytic and (hemi-)cellulolytic genes in aspergilli", Journal of General and Applied Microbiology, Feb. 2001, vol. 47, No. 1, pp. 1-19.
Terabayashi et al., "Identification and characterization of genes responsible for biosynthesis of kojic acid, an industrially important compound from Aspergillus oryzae", Fungal Genetics and Biology, San Diego, CA, US, Dec. 1, 2010, vol. 47, No. 12, pp. 953-961.

* cited by examiner

*Primary Examiner* — Christian L Fronda
(74) *Attorney, Agent, or Firm* — Carrier Blackman & Associates, P.C.; Joseph P. Carrier; Fulchand P. Shende (57) ABSTRACT

To provide a base sequence for protein expression that can increase the yield of protein such as diastatic enzyme by further activating a promoter of a particular gene. A base sequence 1 for protein expression includes: a gene 3 encoding protein 2; a promoter 4 of the gene 3, the promoter being linked upstream of the gene 3; and a cis element 5 whose activity is improved by an artificial transcription factor 6, the cis element being linked further upstream of the promoter 4. The cis element 5 is represented by SEQ ID NO: 1.

20 Claims, 3 Drawing Sheets
Specification includes a Sequence Listing.

NUCLEIC ACID SEQUENCE FOR PROTEIN EXPRESSION

TECHNICAL FIELD

The present invention relates to a base sequence for protein expression for use in the production of protein such as diastatic enzyme using koji mold, and a method for producing protein using the same.

BACKGROUND ART

Heretofore, it has been known that a base sequence for protein expression in which a cis element consisting of a particular base sequence is linked to a promoter of a particular gene that yields protein, when producing protein such as a diastatic enzyme using koji mold (see e.g., Patent Literatures 1 and 2). The conventional base sequence for protein expression can improve the activity of the promoter and can increase the yield of the protein, by linking the cis element to the promoter.

For example, Patent Literature 1 describes a technique of using enhancer DNA consisting of a XlnR/Ace2 binding sequence and a Hap complex binding sequence as a cis element and linking 12 cis elements upstream (on the 5'-terminal side) of a promoter of tef1 gene. According to Patent Literature 1, in this way, GUS activity by the promoter is reported to be improved approximately 4.9 times under solid culture conditions with wheat bran as a carbon source.

Also, Patent Literature 2 describes a technique of using enhancer DNA located at a promoter of α-glucosidase gene of koji mold (*Aspergillus oryzae*) as a cis element and linking 12 such cis elements upstream (on the 5'-terminal side) of the promoter. According to Patent Literature 2, in this way, GUS activity by the promoter is reported to be improved approximately 6 times under culture conditions with starch as a carbon source.

CITATION LIST

Patent Literature

[PTL 1]
Japanese Patent Application Laid-Open No. 2012-75369
[PTL 2]
Japanese Patent No. 3343567

SUMMARY OF INVENTION

Technical Problem

However, the conventional base sequence for protein expression merely links a cis element consisting of a particular base sequence to a promoter of a particular gene and is thus desired to be further modified.

In light of these circumstances, an object of the present invention is to provide a base sequence for protein expression that can increase the yield of protein such as diastatic enzyme by further activating a promoter of a particular gene, and a method for producing protein using the same.

Solution to Problem

In order to attain the object, the base sequence for protein expression of the present invention is a base sequence for protein expression comprising: a gene encoding protein; a promoter of the gene, the promoter being linked upstream of the gene; and a cis element whose activity is improved by an artificial transcription factor, the cis element being linked further upstream of the promoter, wherein the cis element is represented by SEQ ID NO: 1.

According to the base sequence for protein expression of the present invention, the activity of the cis element represented by SEQ ID NO: 1 linked upstream of the promoter can be improved by the artificial transcription factor, and the activity of the promoter can be further improved by the cis element whose activity has been improved. As a result, the activity of the gene is improved by the promoter whose activity has been improved, so that the yield of the protein encoded by the gene can be increased.

In the base sequence for protein expression of the present invention, the artificial transcription factor comprises a DNA binding domain comprising a base sequence of upstream 1 to 118 aa of a transcription factor KojR and an active domain comprising a base sequence of downstream 113 to 604 aa of a transcription factor AmyR, and the active domain is linked downstream of the DNA binding domain, and is represented by SEQ ID NO: 2 The artificial transcription factor represented by SEQ ID NO: 2 can improve the activity of the cis element.

The base sequence for protein expression of the present invention preferably comprises a base sequence for artificial transcription factor expression comprising: a gene encoding the artificial transcription factor represented by SEQ ID NO: 2; and a promoter of the gene, the promoter being linked upstream of the gene. According to the base sequence for artificial transcription factor expression, the activity of the gene encoding the artificial transcription factor represented by SEQ ID NO: 2 is improved by the promoter of the gene so that the artificial transcription factor encoded by the gene is produced.

For the base sequence for protein expression of the present invention, it is required that at least one cis element represented by SEQ ID NO: 1 should be linked upstream of the promoter. Preferably, the cis element is linked, for example, at any number in a range of 1 to 10, upstream of the promoter.

The expression vector of the present invention comprises the base sequence for protein expression of the present invention. According to the expression vector of the present invention, a transformant comprising the base sequence for protein expression of the present invention can be produced.

The transformant of the present invention comprises the base sequence for protein expression of the present invention. According to the transformant of the present invention, the yield of the protein encoded by the gene can be increased.

For the transformant of the present invention, it is preferred that koji mold should be used as a host cell, and it is more preferred that the koji mold should be an *Aspergillus oryzae* HO2strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01750).

The method for producing a protein according to the present invention comprises culturing a transformant comprising the base sequence for protein expression of the present invention, and recovering the protein encoded by the gene expression-enhanced by the base sequence for protein expression, from the medium or the inside of the transformant after the culture.

The base sequence for protein expression of the present invention can increase the yield of the protein encoded by the gene, as mentioned above. Accordingly, when the transformant comprising the base sequence for protein expression of the present invention is cultured, the produced protein accumulates in the medium or the transformant after the culture. Therefore, the protein can be recovered.

DESCRIPTION OF EMBODIMENTS

Next, the embodiments of the present invention will be described further specifically with reference to the attached drawings.

Figure 1:
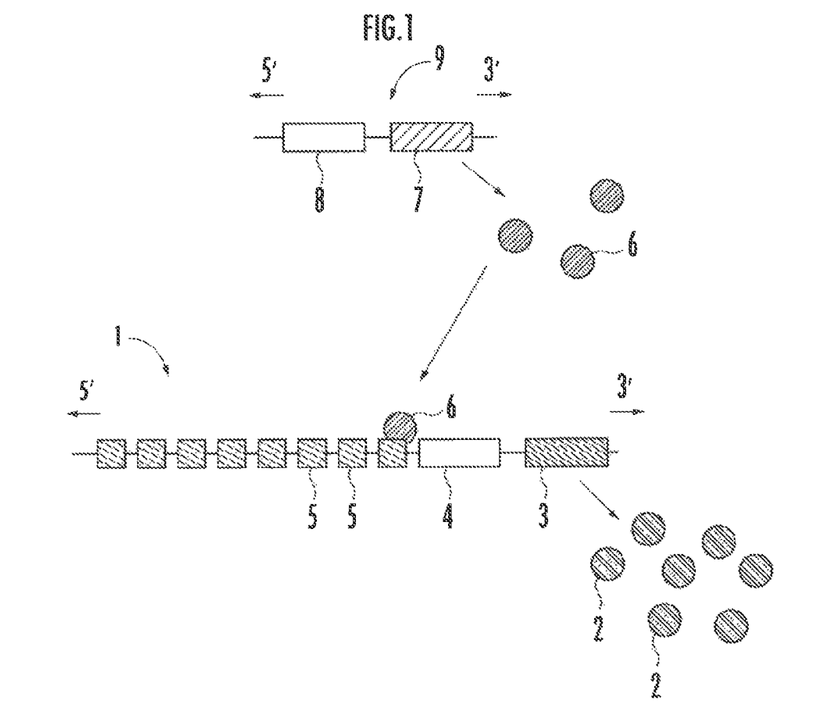
FIG. 1 is an illustrative diagram schematically showing the configuration and effect of a base sequence for protein expression of the present invention.

As shown in FIG. 1, a base sequence 1 for protein expression of the present embodiment comprises: a protein gene 3 encoding a desired protein 2; a promoter 4 linked upstream (on the 5'-terminal side) of the protein gene 3; and a cis element 5 linked upstream (on the 5'-terminal side) of the promoter 4.

The protein 2 is, for example, a diastatic enzyme. The protein gene 3 may be any gene which encodes the protein 2.

The cis element 5 is composed of a base sequence comprising enhancer DNA located at a promoter of kojT gene, and the base sequence is gacggaaaagtcgggtagat (SEQ ID NO: 1). In the base sequence 1 for protein expression, 1 to 10, for example, 8 cis elements 5 are linked upstream of the promoter 4.

The base sequence 1 for protein expression also comprises a base sequence 9 for artificial transcription factor expression comprising: an artificial transcription factor gene 7 encoding an artificial transcription factor 6; and a promoter 8 linked upstream (on the 5'-terminal side) of the artificial transcription factor gene 7. The activity of the cis element 5 is improved by the artificial transcription factor 6.

Figure 2:
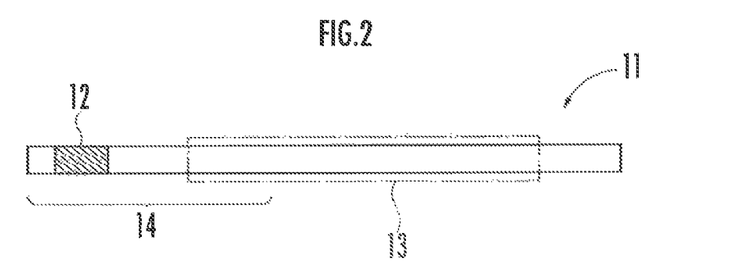
FIG. 2 is an illustrative diagram schematically showing a predicted structure of a transcription factor KojR.
Figure 3:
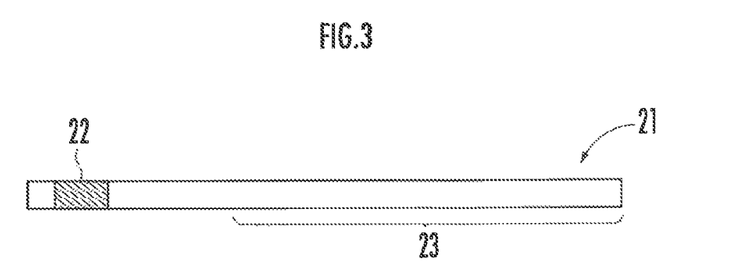
FIG. 3 is an illustrative diagram schematically showing a predicted structure of a transcription factor AmyR.

The artificial transcription factor 6 is prepared from a transcription factor KojR 11 shown in FIG. 2 and a transcription factor AmyR 21 shown in FIG. 3. The transcription factors KojR 11 and AmyR 21 are transcription factors both classified into Cys6 cysteine-Zinc cluster type, among transcription factors having a zinc-coordinating DNA binding domain (Zn_Cluster).

As shown in FIG. 2, the transcription factor KojR 11 comprises upstream (5'-terminal side) Zn_Cluster 12 and comprises downstream (3'-terminal side) MHR 13 which is a highly homologous region common in transcription factors classified in Cys6 cysteine-Zinc cluster type. In this context, the transcription factor KojR 11 is composed of a base sequence of 555 aa in full length. The Zn_Cluster 12 is composed of a base sequence of 15 to 45 aa. The MHR 13 is composed of a base sequence of 148 to 281 aa.

In the transcription factor KojR 11, a DNA binding domain associated with binding to the cis element 5 is predicted to reside in a region 14 comprising the upstream Zn_Cluster 12. Examples of a candidate region of the DNA binding domain can include a region composed of a base sequence of 1 to 118 aa, a region composed of a base sequence of 1 to 195 aa, and a region composed of a base sequence of 1 to 239 aa.

On the other hand, as shown in FIG. 3, the transcription factor AmyR 21 comprises upstream (5'-terminal side) Zn_Cluster 22 and comprises a downstream (3'-terminal side) region 23 comprising an active domain. In this context, the transcription factor AmyR 21 is composed of a base sequence of 604 aa in full length. The Zn_Cluster 22 is composed of a base sequence of 13 to 52 aa.

Examples of a candidate region of the active domain in the transcription factor AmyR 21 can include a region composed of a base sequence of 113 to 604 aa, a region composed of a base sequence of 150 to 604 aa, a region composed of base sequence of 219 to 604 aa, and a region composed of a base sequence of 257 to 604 aa.

Accordingly, the artificial transcription factor of the present embodiment has a configuration (SEQ ID NO: 2) in which an active domain comprising a base sequence of downstream 113 to 604 aa of the transcription factor AmyR is linked downstream of a DNA binding domain comprising a base sequence of upstream 1 to 118 aa of the transcription factor KojR.

According to the base sequence 1 for protein expression of the present embodiment, as shown in FIG. 1, the artificial transcription factor 6 encoded by the artificial transcription factor gene 7 whose activity has been improved by the promoter 8 in the base sequence 9 for artificial transcription factor expression is produced, and the produced artificial transcription factor 6 binds to the cis element 5. The activity of the cis element 5 is improved by the binding to the artificial transcription factor 6. The activity of the promoter 4 is improved by the cis element 5 whose activity has been improved.

Then, the activity of the protein gene 3 is improved by the promoter 4 whose activity has been improved, so that the protein 2 encoded by the protein gene 3 whose activity has been improved, is produced. As a result, the base sequence 1 for protein expression of the present embodiment can increase the yield of the protein 2. Next, Examples of the present invention will be shown.

Example 1

(Construction of Transformant Introduced with Artificial Transcription Factor Gene)

In this Example, first, the genomic DNA gene of an *Aspergillus oryzae* HO2strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01750) was used as a template in PCR to amplify an upstream sequence of tppA gene using primers 1 and 2, its downstream sequence using primers 3 and 4, a tef1 promoter gene using primers 5 and 6, anagdA terminator gene using primers 7 and 8, and a gene fragment for marker recycling using primers 9 and 10, while the genomic DNA gene of an *Aspergillus awamori* HA1strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01751) was used as a template in PCR to amplify a gene cassette for pyrG gene expression using primers 11 and 12. DNA polymerase (manufactured by Toyobo Co., Ltd., product name: KOD FX neo) was used in each PCR amplification. The amplification products were each purified using a purification kit (manufactured by Qiagen N.V., product name: QIAquick PCR purification kit) to obtain a total of 6 gene fragments.

Next, an *E. coli*-derived plasmid pMD20 (manufactured by Takara Bio Inc.) was used as a template in PCR to amplify a gene fragment derived from the plasmid using primers 13 and 14 and the DNA polymerase. The amplification product was purified using the purification kit to obtain the gene fragment.

Next, these 7 gene fragments were sequentially treated with a cloning kit (manufactured by Takara Bio Inc., product name: In-Fusion HD Cloning kit) and used in the transformation of an *E. coli* HST08strain (manufactured by Takara Bio Inc.) to construct a plasmid pPT.

Next, the plasmid pPT was treated with a restriction enzyme SmaI (manufactured by Takara Bio Inc.) at 30° C. and purified using the purification kit to obtain the restriction treatment product of the plasmid (gene fragment).

Next, the genomic DNA gene of an *Aspergillus oryzae* HO2 strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01750) was used as a template in PCR to amplify a DNA binding domain of a transcription factor KojR using primers 15 and 16 and an active domain of a transcription factor AmyR using primers 17 and 18. The DNA polymerase AmyR was used in each PCR amplification. The amplification products were each purified using the purification kit to obtain the DNA binding domain and the active domain.

Next, the DNA binding domain and the active domain were treated with the cloning kit and used in the transformation of an *E. coli* HST08strain to construct a plasmid carrying an artificial transcription factor gene in which the DNA binding domain and the active domain were joined together.

The plasmid carrying the artificial transcription factor gene was used as a template in PCR to amplify a gene fragment for koji mold transformation using primers 19 and 20 using DNA polymerase (manufactured by Toyobo Co., Ltd., product name: KOD-plus-neo). The amplification product was purified using the purification kit to obtain the gene fragment for koji mold transformation.

Next, an *Aspergillus oryzae* HO2strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01750) was transformed with the gene fragment for koji mold transformation according to the standard method of the PEG-calcium technique. Subsequently, the obtained transformants were screened for a strain capable of growing in a CD plate medium to obtain a transcription factor-producing strain.

Next, the transcription factor-producing strain was inoculated at $1\times10^6$ cells/plate to a CD medium supplemented with fluoroorotic acid monohydrate (manufactured by Wako Pure Chemical Industries, Ltd.) (final concentration: 1 mg/mL) and uridine (manufactured by Sigma-Aldrich Inc.) (final concentration: 20 mM) and screened for a strain capable of growing therein to obtain a uridine-auxotrophic transcription factor-producing strain.

The base sequences of the primers 1 to 20 are shown in Table 1.

TABLE 1

| Primer No. | Base sequence 5'→3' | SEQ ID NO | Remarks |
|---|---|---|---|
| 1 | ccggctcgtatgttgctggaccaaccgccaaggttag | 3 | Upstream sequence of tppA gene |
| 2 | actgaattgcaattaatggcggacaatg | 4 | Upstream sequence of tppA gene |
| 3 | tgtctcggaccttacgtgtcttagatgcgactcaatacaactgttc | 5 | Downstream sequence of tppA gene |
| 4 | tgggtaacgccagggttgaggctgaagacttaaatacgacattgc | 6 | Downstream sequence of tppA gene |
| 5 | ctgttacgcttccccgggtttgaaggtggtgcgaactttgtagttc | 7 | tef1 promoter gene |
| 6 | gtaaggtccgagacagtaagggattgatc | 8 | tef1 promoter gene |
| 7 | taattgcaattcagtagtaacccattcccggttctctagctg | 9 | agdA terminator gene |
| 8 | gtaacgccagggcccggggaagcgtaacaggatagcctagaccac | 10 | agdA terminator gene |
| 9 | ctgcaggatgattagcgtgcaaaccaagcaaacaagcatc | 11 | Gene fragment for marker recycling |
| 10 | actgaattgcaattaatggcggacaatg | 12 | Gene fragment for marker recycling |
| 11 | taattgcaattcagtgcaagctcgagcatccaactaaactag | 13 | Gene cassette for pyrG gene expression |
| 12 | tgggtaacgccagggcccgggctaatcatcctgcagctccgtcattg | 14 | Gene cassette for pyrG gene expression |

TABLE 1-continued

| Primer No. | Base sequence 5'→3' | SEQ ID NO | Remarks |
|---|---|---|---|
| 13 | ccctggcgttacccaacttaatcg | 15 | Plasmid-derived gene fragment |
| 14 | caacatacgagccggaagcataaagtg | 16 | Plasmid-derived gene fragment |
| 15 | cgcaccaccttcaaaatgtcgttgaataccgacgattccggtc | 17 | DBD of transcription factor kojR |
| 16 | acctaggttccagctaaacccgtacac | 18 | DBD of transcription factor kojR |
| 17 | atcctgttacgcttctcaaaacgaaatctcctccccagcc | 19 | AD of transcription factor AmyR |
| 18 | agctggaacctaggtgcccagtatctacatccagacttctcg | 20 | AD of transcription factor AmyR |
| 19 | cagtgagcgcaacgcaattaatgtgagttag | 21 | Gene fragment for koji mold transformation |
| 20 | gggatgtgctgcaaggcgattaagttg | 22 | Gene fragment for koji mold transformation |

[Construction of GUS-Producing Strain with Cis Elements Linked]

First, a first gene fragment in which: 4 cis elements of SEQ ID NO: 1 were linked in tandem; restriction enzyme sites SphI and BamHI were added on the 5'-terminal side thereof; and BglII and NcoI sites were added on the 3'-terminal side thereof was prepared by oligo synthesis.

Next, the first gene fragment and a plasmid pPEA2 containing an *Aspergillus oryzae*-derived enoA promoter were each fragmented by treatment with restriction enzymes SphI and NcoI. These fragments were subjected to ligation reaction, and *E. coli* was then transformed with the ligation product to construct a plasmid pEA4K.

Next, the gene fragment was treated with a restriction enzyme BamHI, while the plasmid pEA4K was treated with restriction enzymes BglII and NcoI. These two treatment products were subjected to ligation reaction, and *E. coli* was then transformed with the ligation product to construct a plasmid pEA8K.

Next, the plasmid pEA8K was used as a template in PCR amplification using primers 21 and 22 and DNA polymerase (manufactured by Toyobo Co., Ltd., product name: KOD-plus-). The amplification product was purified using a purification kit (manufactured by Promega Corp., product name: Wizard SV Gel and PCR Clean-Up System) to obtain a second gene fragment.

Next, the genomic DNA of *Aspergillus oryzae* was used as a template in PCR amplification using primers 23 and 24 and DNA polymerase (manufactured by Toyobo Co., Ltd., product name: KOD-plus-). The amplification product was purified using a purification kit (manufactured by Promega Corp., product name: Wizard SV Gel and PCR Clean-Up System) to obtain a third gene fragment.

Next, the second gene fragment and the third gene fragment were used as a template in fusion PCR using primers 22 and 24 to prepare a fourth gene fragment in which the second gene fragment and the third gene fragment were joined together.

Next, a restriction enzyme-treated plasmid pPPG introduced with an *E. coli*-derived plasmid pMD20 (manufactured by Takara Bio Inc.) carrying upstream 1000 bp of *Aspergillus oryzae*-derived pyrG gene, an *Aspergillus oryzae*-derived pyrG expression cassette, and an *E. coli*-derived uidA gene was subjected to ligation reaction with a gene fragment for marker recycling obtained by PCR-amplifying a plasmid pPPG as a template using primers 25 and 26 and DNA polymerase (manufactured by Toyobo Co., Ltd., product name: KOD-plus-) and purifying the amplification product using a purification kit (manufactured by Promega Corp., product name: Wizard SV Gel and PCR Clean-Up System). Then, *E. coli* was transformed with the ligation product to construct a plasmid pPPRG.

Next, the plasmid pPPRG was used as a template in PCR amplification using primers 27 and 28 and DNA polymerase (manufactured by Toyobo Co., Ltd., product name: KOD-plus-). The amplification product was purified using a purification kit (manufactured by Promega Corp., product name: Wizard SV Gel and PCR Clean-Up System) to obtain a fifth gene fragment.

The fourth gene fragment and the fifth gene fragment were used as a template in fusion PCR using primers 24 and 27 to prepare a cis element-linked GUS (β-glucuronidase) production cassette gene fragment in which the fourth gene fragment and the fifth gene fragment were joined together.

Next, the uridine-auxotrophic transcription factor-producing strain was transformed using the cis element-linked GUS production cassette gene fragment according to the standard method of the PEG-calcium technique. Subsequently, the obtained transformants were screened for a strain capable of growing in a CD plate medium to obtain a GUS-producing strain with 8 cis elements linked in tandem.

The base sequences of the primers 21 to 28 are shown in Table 2.

TABLE 2

| Primer No. | Base sequence 5'→3' | SEQ ID NO |
|---|---|---|
| 21 | ccgctgctaggcgcgccgtgcactatagggcgaattgggc | 23 |
| 22 | tggggtttctacaggacgtaacattttgacgagctgcggaattg | 24 |
| 23 | cacggcgcgcctagcagcgggtagtggtggatacgtactcctt | 25 |
| 24 | ttcaggtcacgttctaagcttatcag | 26 |
| 25 | ccccctccggatgatgtagaagttgctcggtagctg | 27 |
| 26 | ccccctccggacaattgccgcgaaaaattaaattg | 28 |
| 27 | ccagaggtgactttatccaagatt | 29 |
| 28 | caattccgcagctcgtcaaaatgttacgtcctgtagaaacccca | 30 |

[GUS Activity Measurement Method]

The GUS-producing strain with 8 cis elements linked in tandem was cultured in a CD plate medium for 1 week to form spores. The spores were recovered using 0.01% POLYSORBATE 20 (manufactured by Wako Pure Chemical Industries, Ltd.) to obtain a spore suspension.

Next, 50 mL of a PD medium (2 mass/volume % of dextrin, 1 mass/volume % of polypeptone, 0.1 mass/volume % of casamino acid, 0.5 mass/volume % of potassium dihydrogen phosphate, 0.05 mass/volume % of magnesium sulfate, and 0.1 mass/volume % of sodium nitrate) was placed in a 200 mL Erlenmeyer flask, to which the spores were then inoculated at a final spore concentration of $1 \times 10^5$/mL.

Next, liquid culture was performed at 30° C. for 60 hours. After the completion of the culture, the bacterial cells were disrupted, and the disrupted powder was suspended in a buffer for intracellular protein extraction having the composition given below to obtain an extract.

| [Composition of buffer for intracellular protein extraction] | |
|---|---|
| $NaH_2PO_4 \cdot 2H_2O$ (MW = 156.01) (pH 7) | 1.56 g (50 mM) |
| 0.5M EDTA | 4 mL (10 mM) |
| Nonionic surfactant (manufactured by Sigma-Aldrich Inc., product name: Triton X-100) | 0.2 g (0.1%) |
| N-LaurylsarcosinateNa | 0.2 g (0.1%) |
| β-mercaptoethanol (MW = 78.13) | 142 μL (10 mM) |
| Distilled water | 200 mL |

Next, the extract was added to a buffer for GUS activity measurement having the composition given below and reacted at 37° C. for 15 minutes. Then, the absorbance was measured at a wavelength of 415 nm to calculate an activity value (U). 1 U means the amount of the enzyme necessary for forming 1 mM PNP from PNP-Glucuronide (purine nucleoside phosphorylase-glucuronic acid inclusion) at 37° C. for 1 minute.

| [Composition of buffer for GUS activity measurement] | |
|---|---|
| $NaH_2PO_4 \cdot 2H_2O$ (MW = 156.01) (pH 7) | 1.56 g (50 mM) |
| β-mercaptoethanol (MW = 78.13) | 142 μL (10 mM) |
| Nonionic surfactant (manufactured by Sigma-Aldrich Inc., product name: Triton X-100) | 0.2 g (0.1%) |
| p-Nitrophenyl β-D-glucuronic acid inclusion (MW = 315.23) | 63 mg (1 mM) |
| Distilled water | 200 mL |

Next, the amount of the protein contained in the extract was measured using protein assay CBB solution (manufactured by NacalaiTesque, Inc.), and the activity value was divided by the amount of the protein to calculate GUS activity (U/mg). The results are shown as a relative value of GUS activity in FIG. 4.

Figure 5:
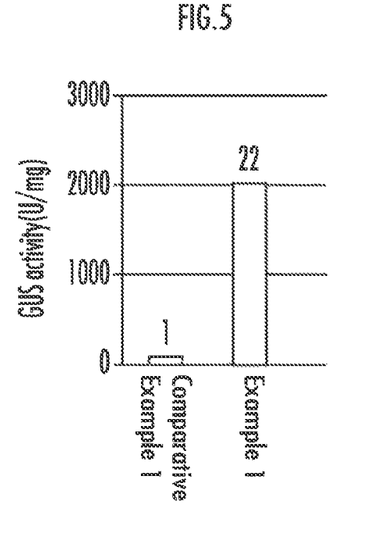
FIG. 5 is a graph showing GUS activity when the transformant of the present invention was cultured for 90 hours with dextrin as the substrate.

Also, GUS activity (U/mg) when the liquid culture was performed at 30° C. for 90 hours is shown in FIG. 5.

Comparative Example 1

In this Comparative Example, a GUS-producing strain was constructed in totally the same way as in Example 1 except that the artificial transcription factor gene was not introduced and no cis element was linked.

Next, GUS activity was measured in totally the same way as in Example 1 except that the GUS-producing strain obtained in this Comparative Example was used.

Figure 4:
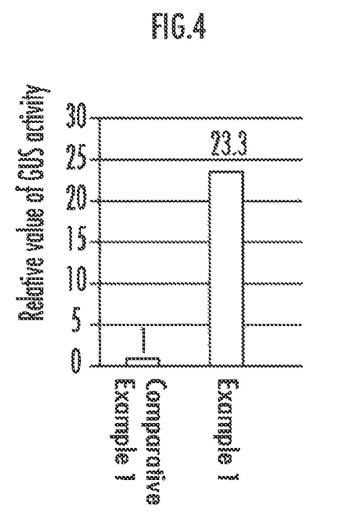
FIG. 4 is a graph showing a relative value of GUS activity when a transformant of the present invention was cultured for 60 hours with dextrin as a substrate.

A relative value of GUS activity (U/mg) when the liquid culture was performed at 30° C. for 60 hours is shown in FIG. 4. GUS activity (U/mg) when the liquid culture was performed at 30° C. for 90 hours is shown in FIG. 5.

From FIG. 4, when the GUS activity (U/mg) in which the liquid culture was performed at 30° C. for 60 hours with dextrin as a substrate is defined as 1 for the GUS-producing strain of Comparative Example 1 in which the artificial transcription factor gene was not introduced and no cis element was linked, it is obvious that 23.3 times GUS activity can be obtained in the GUS-producing strain of Example 1.

From FIG. 5, when the GUS activity (U/mg) when the liquid culture was performed at 30° C. for 90 hours with dextrin as a substrate is defined as 1 for the GUS-producing strain of Comparative Example 1 in which the artificial transcription factor gene was not introduced and no cis element was linked, it is obvious that 22 times GUS activity can be obtained in the GUS-producing strain of Example 1.

Example 2

In this Example, GUS activity (U/mg) was calculated in totally the same way as in Example 1 except that 50 mL of a PG medium (2 mass/volume % of glucose, 1 mass/volume % of polypeptone, 0.1 mass/volume % of casamino acid, 0.5 mass/volume % of potassium dihydrogen phosphate, 0.05 mass/volume % of magnesium sulfate, and 0.1 mass/volume % of sodium nitrate) was placed in a 200 mL Erlenmeyer flask, to which the spores of the GUS-producing strain harboring 8 cis elements linked in tandem obtained in Example 1 were then inoculated at a final spore concentration of 1×10⁵/mL, followed by liquid culture at 30° C. for 60 hours. The results are shown in FIG. 6.

Comparative Example 2

In this Comparative Example, GUS activity was measured in totally the same way as in Example 2 except that the GUS-producing strain obtained in Comparative Example 1 was used. GUS activity (U/mg) when the liquid culture was performed at 30° C. for 60 hours is shown in FIG. 6.

Figure 6:
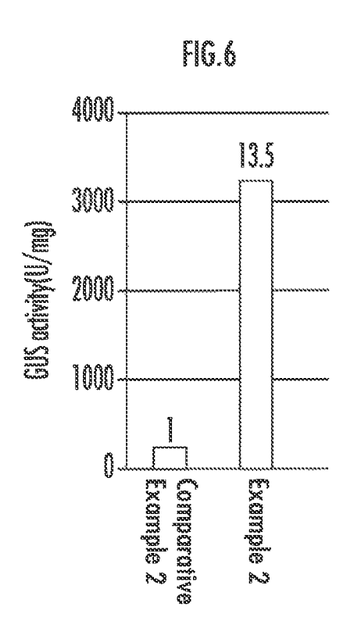
FIG. 6 is a graph showing GUS activity when the transformant of the present invention was cultured for 60 hours with glucose as a substrate.

From FIG. 6, when the GUS activity (U/mg) in which the liquid culture was performed at 30° C. for 60 hours with glucose as a substrate is defined as 1 for the GUS-producing strain of Comparative Example 2 in which the artificial transcription factor gene was not introduced and no cis element was linked, it is obvious that 13.5 times GUS activity can be obtained in the GUS-producing strain of Example 2.

REFERENCE SIGNS LIST 1 base sequence for protein expression
2 protein
3 gene
4 promoter
5 cis element
6 artificial transcription factor

---

Sequence Listing
SEQUENCE LISTING

<110>   HONDA MOTOR CO., LTD.

<120>   Base sequence for protein expression and production of protein

<130>   PCT160079

<160>   30

<170>   PatentIn version 3.5

<210>   1
<211>   20
<212>   DNA
<213>   Aspergillusoryzae

<400>   1
gacggaaaagtcgggtagat                                                        20

<210>   2
<211>   1983
<212>   DNA
<213>   Aspergillusoryzae

<400>   2
atgtcgttgaataccgacgattccggtcggataaggacccggcaacgcgccaaaagagcg                60 tgcgaaacgtgcaaactgcgcaagaggaaatgtgacggccatgagccctgcacttactgc               120 ttgcgatacgaatatcagtgcactttcaagcctcatccacggagaaagcctgcagcttcc               180 aaatcttccgcacggcccagcgaggaagaagactcaccaaagtttctcgacagagttgat               240 gctaaccaagaacacatggaggccaactcaggcaccgctttcccccatctcctagggatg               300 aggttgaacccgcagggtgctcccaaggtgtacgggtttagctggaacctaggtgcccag               360 tatctacatccagacttctcggagtcgttcactcgactaccaccccagatctcgtctcc                420 tctcccgactcgacaaactcgctattcgactcgtccactatcggcgcactcccgcgcca                480 cgccgtctgtcgacgccaaaccttctagcccatgtcaatgtcttcctcaagtacctgttc               540 ccgatcatgcccgtcgtgagacaggaccagctgcagcaggactgccaccagccggagcgc               600 ttgtctccccaacgctacgctttcattgccgctctatgcgcggccacgcacatccaactg               660 aagctggacggtgcagcaccgggtcccgaggcggcttccgcgcgagccagcctcgacgga               720 catcctatgttgtcgggagaagaactcctggctgaagccgtgcgcgcaagaaaggaatac               780 aacgtggtcgacgaaattaacatggaaaacctcctaacctccttctttctcttcgccgcc               840 tacggaaacctagacagacaggatcaggcctggttctacctatgtcagaccacgtccatg               900 gtcttcacactaggcctacaacgggaatccacatactcgaaactaagcgtcgaggaagca               960 gaagagaaaggagagtattctggctcttattcgtcacagaaaggtaagaaaagaaaaaa               1020 ctctactttcccaatcaccaccacgtaccaaaaataacacgaaaaaccagaggctacgca               1080

```
                         Sequence Listing
                         SEQUENCE LISTING ttacaacaagcaaaaccagtcatgctccgcaactccatccacaaaccacaggtcctgtgc      1140 tcagacgacccaatcctagcctacggcttcatcaacctcatcaacgtcttcgaaaagctc     1200 agcccaaatctctacgactgggtctccgccggcggcagcagcgcagacggcgaccccccg     1260 cctacttcttctatccaatccagtctcgccaagcaaatctccctcgagggcgtctccgag     1320 atccagaaagtagacatcctcatcactcagcaatggctacaaaccatgatgtggaaactc    1380 tccatgacccacgtcacacagcccggctctcgcgatgacgccgttctccccttccacctg    1440 cccgtgctagtcggcaaggccgtcatgggcgtcatcgccgcggcatcccaaggtgctgtt    1500 gacgctcatggtatcggaatggtaagaaagcgaccttacctcatcacaccctccctcatc    1560 agtcactccccatcatctataccgcaatctaacaaaaaccgcaggaacaaaaactctac     1620 gacctcggcacctccgtagccgacgtctcccgctccctaagcacaaaagccgccaccac    1680 ctcgccgaatcgaccatcgaccccgagaactcctctggggcattctcacaaccctatcc    1740 cgaatccgcggttcccaatcatacctcttcccagcgctcgtcgagcaaagtcgaggcatc    1800 atcagtttcgactgttcgctttccatcagtgactttctgccttcgtttggtgggccgccg    1860 gctattatgtggcggacgggtgaatctgggtttgatttattggggatcgcggatgatttg    1920 caagagagggagaatgagggtggggaggggattgtggtggctggggaggagatttcgttt    1980 tga                                                              1983

<210>   3
<211>   37
<212>   DNA
<213>   Aspergillusoryzae

<400>   3
ccggctcgtatgttgctggaccaaccgccaaggttag                            37

<210>   4
<211>   28
<212>   DNA
<213>   Aspergillusoryzae

<400>   4
actgaattgcaattaatggcggacaatg                                     28

<210>   5
<211>   46
<212>   DNA
<213>   Aspergillusoryzae

<400>   5
tgtctcggaccttacgtgtcttagatgcgactcaatacaactgttc                   46

<210>   6
<211>   45
<212>   DNA
<213>   Aspergillusoryzae

<400>   6
tgggtaacgccagggttgaggctgaagacttaaatacgacattgc                    45

<210>   7
<211>   46
<212>   DNA
<213>   Aspergillusoryzae

<400>   7
ctgttacgcttccccgggtttgaaggtggtgcgaactttgtagttc                   46

<210>   8
<211>   29
```

SEQUENCE LISTING

```
<212>   DNA
<213>   Aspergillusoryzae

<400>   8
gtaaggtccgagacagtaagggattgatc                                          29

<210>   9
<211>   42
<212>   DNA
<213>   Aspergillusoryzae

<400>   9
taattgcaattcagtagtaacccattcccggttctctagctg                             42

<210>   10
<211>   46
<212>   DNA
<213>   Aspergillusoryzae

<400>   10
gtaacgccagggcccggggaagcgtaacaggatagcctagacccac                         46

<210>   11
<211>   40
<212>   DNA
<213>   Aspergillusoryzae

<400>   11
ctgcaggatgattagcgtgcaaaccaagcaaacaagcatc                               40

<210>   12
<211>   28
<212>   DNA
<213>   Aspergillusoryzae

<400>   12
actgaattgcaattaatggcggacaatg                                           28

<210>   13
<211>   42
<212>   DNA
<213>   Aspergillusawamorii

<400>   13
taattgcaattcagtgcaagctcgagcatccaactaaact ag                            42

<210>   14
<211>   47
<212>   DNA
<213>   Aspergillusawamorii

<400>   14
tgggtaacgccagggcccgggctaatcatcctgcagctccgtcattg                        47

<210>   15
<211>   24
<212>   DNA
<213>   Escherichia coli

<400>   15
ccctggcgttacccaacttaatcg                                               24

<210>   16
<211>   27
<212>   DNA
<213>   Escherichia coli

<400>   16
caacatacgagccggaagcataaagtg                                            27

<210>   17
<211>   43
```

Sequence Listing
SEQUENCE LISTING

```
<212>    DNA
<213>    Aspergillusoryzae

<400>    17
cgcaccaccttcaaaatgtcgttgaataccgacgattccggtc                    43

<210>    18
<211>    27
<212>    DNA
<213>    Aspergillusoryzae

<400>    18
acctaggttccagctaaacccgtacac                                    27

<210>    19
<211>    40
<212>    DNA
<213>    Aspergillusoryzae

<400>    19
atcctgttacgcttctcaaaacgaaatctcctccccagcc                       40

<210>    20
<211>    42
<212>    DNA
<213>    Aspergillusoryzae

<400>    20
agctggaacctaggtgcccagtatctacatccagacttct cg                    42

<210>    21
<211>    31
<212>    DNA
<213>    Aspergillusoryzae

<400>    21
cagtgagcgcaacgcaattaatgtgagtta g                               31

<210>    22
<211>    27
<212>    DNA
<213>    Aspergillusoryzae

<400>    22
gggatgtgctgcaaggcgattaagttg                                    27

<210>    23
<211>    40
<212>    DNA
<213>    Aspergillusoryzae

<400>    23
ccgctgctaggcgcgccgtgcactatagggcgaattgggc                       40

<210>    24
<211>    44
<212>    DNA
<213>    Aspergillusoryzae

<400>    24
tggggtttctacaggacgtaacattttgacgagctgcggaattg                   44

<210>    25
<211>    43
<212>    DNA
<213>    Aspergillusoryzae

<400>    25
cacggcgcgcctagcagcgggtagtggtggatacgtactcctt                    43

<210>    26
<211>    26
```

Sequence Listing

SEQUENCE LISTING

```
<212>   DNA
<213>   Aspergillusoryzae

<400>   26
ttcaggtcacgttctaagcttatcag                                              26

<210>   27
<211>   37
<212>   DNA
<213>   Aspergillusoryzae

<400>   27
ccccctccggatgatgtagaagttgctcggtagctg                                    37

<210>   28
<211>   36
<212>   DNA
<213>   Aspergillusoryzae

<400>   28
ccccctccggacaattgccgcgaaaaattaaattg                                     36

<210>   29
<211>   24
<212>   DNA
<213>   Aspergillusoryzae

<400>   29
ccagaggtgactttatccaagatt                                                24

<210>   30
<211>   44
<212>   DNA
<213>   Aspergillusoryzae

<400>   30
caattccgcagctcgtcaaaatgttacgtcctgtagaaacccca                            44
```

SEQUENCE LISTING

```
<160> NUMBER OF SEQ ID NOS: 30

<210> SEQ ID NO 1
<211> LENGTH: 20
<212> TYPE: DNA
<213> ORGANISM: Aspergillus oryzae

<400> SEQUENCE: 1
gacggaaaag tcgggtagat                                                   20

<210> SEQ ID NO 2
<211> LENGTH: 1983
<212> TYPE: DNA
<213> ORGANISM: Aspergillus oryzae

<400> SEQUENCE: 2
atgtcgttga ataccgacga ttccggtcgg ataaggaccc ggcaacgcgc caaaagagcg       60
tgcgaaacgt gcaaactgcg caagaggaaa tgtgacggcc atgagccctg cacttactgc      120
ttgcgatacg aatatcagtg cactttcaag cctcatccac ggagaaagcc tgcagcttcc      180
aaatcttccg cacggcccag cgaggaagaa gactcaccaa agtttctcga cagagttgat      240
gctaaccaag aacacatgga ggccaactca ggcaccgctt tcccccatct cctagggatg      300
aggttgaacc cgcagggtgc tcccaaggtg tacgggttta gctggaacct aggtgcccag      360
tatctacatc cagacttctc ggagtcgttc actcgactac cacccccaga tctcgtctcc      420
```

```
tctcccgact cgacaaactc gctattcgac tcgtccacta tcggcgcact ccccgcgcca      480
cgccgtctgt cgacgccaaa ccttctagcc catgtcaatg tcttcctcaa gtacctgttc      540
ccgatcatgc ccgtcgtgag acaggaccag ctgcagcagg actgccacca gccggagcgc      600
ttgtctcccc aacgctacgc tttcattgcc gctctatgcg cggccacgca catccaactg      660
aagctggacg gtgcagcacc gggtcccgag gcggcttccg cgcgagccag cctcgacgga      720
catcctatgt tgtcgggaga agaactcctg gctgaagccg tgcgcgcaag aaaggaatac      780
aacgtggtcg acgaaattaa catggaaaac ctcctaacct ccttctttct cttcgccgcc      840
tacgaaaacc tagacagaca ggatcaggcc tggttctacc tatgtcagac cacgtccatg      900
gtcttcacac taggcctaca cgggaatcc acatactcga aactaagcgt cgaggaagca      960
gaagagaaaa ggagagtatt ctggctctta ttcgtcacag aaaggtaaga aaagaaaaaa     1020
ctctactttc ccaatcacca ccacgtacca aaataacac gaaaaaccag aggctacgca     1080
ttacaacaag caaaaccagt catgctccgc aactccatcc acaaaccaca ggtcctgtgc     1140
tcagacgacc caatcctagc ctacggcttc atcaacctca tcaacgtctt cgaaaagctc     1200
agcccaaatc tctacgactg gtctccgcc ggcggcagca gcgcagacgg cgaccccccg     1260
cctacttctt ctatccaatc cagtctcgcc aagcaaatct ccctcgaggg cgtctccgag     1320
atccagaaag tagacatcct catcactcag caatggctac aaaccatgat gtggaaactc     1380
tccatgaccc acgtcacaca gcccggctct cgcgatgacg ccgttctccc cttccacctg     1440
cccgtgctag tcggcaaggc cgtcatgggc gtcatcgccg cggcatccca aggtgctgtt     1500
gacgctcatg gtatcggaat ggtaagaaag cgaccttacc tcatcacacc ctccctcatc     1560
agtcactccc catcatctat acccgcaatc taacaaaaac cgcaggaaca aaaactctac     1620
gacctcggca cctccgtagc cgacgtctcc cgctccctaa gcacaaaagc cgcccaccac     1680
ctcgccgaat cgaccatcga cccccagaaa ctcctctggg gcattctcac aaccctatcc     1740
cgaatccgcg gttcccaatc atacctcttc ccagcgctcg tcgagcaaag tcgaggcatc     1800
atcagtttcg actgttcgct ttccatcagt gactttctgc cttcgtttgg tgggccgccg     1860
gctattatgt ggcggacggg tgaatctggg tttgatttat tggggatcgc ggatgatttg     1920
caagagaggg agaatgaggg tggggagggg attgtggtgg ctggggagga gatttcgttt     1980
tga                                                                  1983

<210> SEQ ID NO 3
<211> LENGTH: 37
<212> TYPE: DNA
<213> ORGANISM: Aspergillus oryzae

<400> SEQUENCE: 3
ccggctcgta tgttgctgga ccaaccgcca aggttag                               37

<210> SEQ ID NO 4
<211> LENGTH: 28
<212> TYPE: DNA
<213> ORGANISM: Aspergillus oryzae

<400> SEQUENCE: 4
actgaattgc aattaatggc ggacaatg                                         28

<210> SEQ ID NO 5
<211> LENGTH: 46
<212> TYPE: DNA
```

<213> ORGANISM: Aspergillus oryzae

<400> SEQUENCE: 5
tgtctcggac cttacgtgtc ttagatgcga ctcaatacaa ctgttc              46

<210> SEQ ID NO 6
<211> LENGTH: 45
<212> TYPE: DNA
<213> ORGANISM: Aspergillus oryzae

<400> SEQUENCE: 6
tgggtaacgc cagggttgag gctgaagact taaatacgac attgc               45

<210> SEQ ID NO 7
<211> LENGTH: 46
<212> TYPE: DNA
<213> ORGANISM: Aspergillus oryzae

<400> SEQUENCE: 7
ctgttacgct tccccgggtt tgaaggtggt gcgaactttg tagttc              46

<210> SEQ ID NO 8
<211> LENGTH: 29
<212> TYPE: DNA
<213> ORGANISM: Aspergillus oryzae

<400> SEQUENCE: 8
gtaaggtccg agacagtaag ggattgatc                                 29

<210> SEQ ID NO 9
<211> LENGTH: 42
<212> TYPE: DNA
<213> ORGANISM: Aspergillus oryzae

<400> SEQUENCE: 9
taattgcaat tcagtagtaa cccattcccg gttctctagc tg                  42

<210> SEQ ID NO 10
<211> LENGTH: 46
<212> TYPE: DNA
<213> ORGANISM: Aspergillus oryzae

<400> SEQUENCE: 10
gtaacgccag ggcccgggga agcgtaacag gatagcctag acccac              46

<210> SEQ ID NO 11
<211> LENGTH: 40
<212> TYPE: DNA
<213> ORGANISM: Aspergillus oryzae

<400> SEQUENCE: 11
ctgcaggatg attagcgtgc aaaccaagca aacaagcatc                     40

<210> SEQ ID NO 12
<211> LENGTH: 28
<212> TYPE: DNA
<213> ORGANISM: Aspergillus oryzae

<400> SEQUENCE: 12
actgaattgc aattaatggc ggacaatg                                  28

<210> SEQ ID NO 13
<211> LENGTH: 42

```
<212> TYPE: DNA
<213> ORGANISM: Aspergillus awamorii

<400> SEQUENCE: 13
taattgcaat tcagtgcaag ctcgagcatc caactaaact ag                    42

<210> SEQ ID NO 14
<211> LENGTH: 47
<212> TYPE: DNA
<213> ORGANISM: Aspergillus awamorii

<400> SEQUENCE: 14
tgggtaacgc cagggcccgg gctaatcatc ctgcagctcc gtcattg               47

<210> SEQ ID NO 15
<211> LENGTH: 24
<212> TYPE: DNA
<213> ORGANISM: Escherichia coli

<400> SEQUENCE: 15
ccctggcgtt acccaactta atcg                                       24

<210> SEQ ID NO 16
<211> LENGTH: 27
<212> TYPE: DNA
<213> ORGANISM: Escherichia coli

<400> SEQUENCE: 16
caacatacga gccggaagca taaagtg                                    27

<210> SEQ ID NO 17
<211> LENGTH: 43
<212> TYPE: DNA
<213> ORGANISM: Aspergillus oryzae

<400> SEQUENCE: 17
cgcaccacct tcaaaatgtc gttgaatacc gacgattccg gtc                  43

<210> SEQ ID NO 18
<211> LENGTH: 27
<212> TYPE: DNA
<213> ORGANISM: Aspergillus oryzae

<400> SEQUENCE: 18
acctaggttc cagctaaacc cgtacac                                    27

<210> SEQ ID NO 19
<211> LENGTH: 40
<212> TYPE: DNA
<213> ORGANISM: Aspergillus oryzae

<400> SEQUENCE: 19
atcctgttac gcttctcaaa acgaaatctc ctccccagcc                      40

<210> SEQ ID NO 20
<211> LENGTH: 42
<212> TYPE: DNA
<213> ORGANISM: Aspergillus oryzae

<400> SEQUENCE: 20
agctggaacc taggtgccca gtatctacat ccagacttct cg                   42

<210> SEQ ID NO 21
```

<210> SEQ ID NO 21
<211> LENGTH: 31
<212> TYPE: DNA
<213> ORGANISM: Aspergillus oryzae

<400> SEQUENCE: 21
cagtgagcgc aacgcaatta atgtgagtta g                               31

<210> SEQ ID NO 22
<211> LENGTH: 27
<212> TYPE: DNA
<213> ORGANISM: Aspergillus oryzae

<400> SEQUENCE: 22
gggatgtgct gcaaggcgat taagttg                                    27

<210> SEQ ID NO 23
<211> LENGTH: 40
<212> TYPE: DNA
<213> ORGANISM: Aspergillus oryzae

<400> SEQUENCE: 23
ccgctgctag gcgcgccgtg cactataggg cgaattgggc                      40

<210> SEQ ID NO 24
<211> LENGTH: 44
<212> TYPE: DNA
<213> ORGANISM: Aspergillus oryzae

<400> SEQUENCE: 24
tggggtttct acaggacgta acattttgac gagctgcgga attg                 44

<210> SEQ ID NO 25
<211> LENGTH: 43
<212> TYPE: DNA
<213> ORGANISM: Aspergillus oryzae

<400> SEQUENCE: 25
cacggcgcgc ctagcagcgg gtagtggtgg atacgtactc ctt                  43

<210> SEQ ID NO 26
<211> LENGTH: 26
<212> TYPE: DNA
<213> ORGANISM: Aspergillus oryzae

<400> SEQUENCE: 26
ttcaggtcac gttctaagct tatcag                                     26

<210> SEQ ID NO 27
<211> LENGTH: 37
<212> TYPE: DNA
<213> ORGANISM: Aspergillus oryzae

<400> SEQUENCE: 27 ccccctccg gatgatgtag aagttgctcg gtagctg                          37

<210> SEQ ID NO 28
<211> LENGTH: 36
<212> TYPE: DNA
<213> ORGANISM: Aspergillus oryzae

<400> SEQUENCE: 28 ccccctccg gacaattgcc gcgaaaaatt aaattg                           36

```
<210> SEQ ID NO 29
<211> LENGTH: 24
<212> TYPE: DNA
<213> ORGANISM: Aspergillus oryzae

<400> SEQUENCE: 29
ccagaggtga ctttatccaa gatt                                          24

<210> SEQ ID NO 30
<211> LENGTH: 44
<212> TYPE: DNA
<213> ORGANISM: Aspergillus oryzae

<400> SEQUENCE: 30
caattccgca gctcgtcaaa atgttacgtc ctgtagaaac ccca                    44
```

The invention claimed is:

1. A nucleic acid sequence for protein expression comprising:
   a gene encoding a protein to be expressed;
   a promoter for the gene, the promoter being linked upstream of the gene; and
   a cis element comprising the nucleic acid sequence of SEQ ID NO: 1, whose activity is improved by an artificial transcription factor, the cis element being linked further upstream of the promoter, wherein the artificial transcription factor is encoded by the nucleic acid of SEQ ID NO: 2.

2. The nucleic acid sequence for protein expression according to claim 1, wherein the artificial transcription factor is encoded by the nucleic acid sequence of SEQ ID NO: 2.

3. The nucleic acid sequence for protein expression according to claim 2, wherein the nucleic acid sequence for protein expression comprises a nucleic acid sequence for the artificial transcription factor to be expressed comprising: a gene encoding the artificial transcription factor encoded by the nucleic acid sequence of SEQ ID NO: 2; and a promoter for the gene encoding the artificial transcription factor, the promoter being linked upstream of the gene encoding the artificial transcription factor.

4. The nucleic acid sequence for protein expression according to claim 1, wherein the cis element with any number selected in a range of 1 to 10 is/are linked upstream of the promoter of the gene encoding the protein.

5. An expression vector including a nucleic acid sequence for protein expression, the nucleic acid sequence for protein expression comprising:
   a gene encoding a protein to be expressed;
   a promoter for the gene, the promoter being linked upstream of the gene; and
   a cis element comprising the nucleic acid sequence of SEQ ID NO: 1, whose activity is improved by an artificial transcription factor, the cis element being linked further upstream of the promoter, wherein the artificial transcription factor is encoded by the nucleic acid of SEQ ID NO: 2.

6. The expression vector according to claim 5, wherein the artificial transcription factor is encoded by the nucleic acid sequence of SEQ ID NO: 2.

7. The expression vector according to claim 6, wherein the nucleic acid sequence for protein expression comprises a nucleic acid sequence for the artificial transcription factor to be expressed comprising: a gene encoding the artificial transcription factor encoded by the nucleic acid sequence of SEQ ID NO: 2; and a promoter for the gene encoding the artificial transcription factor, the promoter being linked upstream of the gene encoding the artificial transcription factor.

8. The expression vector according to claim 5, wherein in the nucleic acid sequence for protein expression, the cis element with any number selected in a range of 1 to 10 is/are linked upstream of the promoter of the gene encoding the protein.

9. A transformant including a nucleic acid sequence for protein expression, the nucleic acid sequence for protein expression comprising:
   a gene encoding a protein to be expressed;
   a promoter for the gene, the promoter being linked upstream of the gene; and
   a cis element comprising the nucleic acid sequence of SEQ ID NO: 1, whose activity is improved by an artificial transcription factor, the cis element being linked further upstream of the promoter, wherein the artificial transcription factor is encoded by the nucleic acid of SEQ ID NO: 2.

10. The transformant according to claim 9, wherein the artificial transcription factor is encoded by the nucleic acid sequence of SEQ ID NO: 2.

11. The transformant according to claim 10, wherein the nucleic acid sequence for protein expression comprises a nucleic acid sequence for the artificial transcription factor to be expressed comprising: a gene encoding the artificial transcription factor encoded by the nucleic acid sequence of SEQ ID NO: 2; and a promoter for the gene encoding the artificial transcription factor, the promoter being linked upstream of the gene encoding the artificial transcription factor.

12. The transformant according to claim 9, wherein in the nucleic acid sequence for protein expression, the cis element with any number selected in a range of 1 to 10 is/are linked upstream of the promoter of the gene encoding the protein.

13. The transformant according to claim 9, wherein koji mold is used as a host cell.

14. The transformant according to claim 13, wherein the koji mold is an *Aspergillus oryzae* HO2strain (National Institute of Technology and Evaluation, Patent Microorganisms Depositary, #122, 2-5-8 Kazusakamatari, Kisarazu-shi, Chiba, Japan, Deposition Date: Nov. 12, 2013, Deposition No.: NITE BP-01750).

15. The nucleic acid sequence for protein expression according to claim 1, wherein the nucleic acid sequence for protein expression comprises a nucleic acid sequence for the artificial transcription factor to be expressed comprising: a gene encoding the artificial transcription factor; and a promoter for the gene encoding the artificial transcription factor, the promoter being linked upstream of the gene encoding the artificial transcription factor.

16. The nucleic acid sequence for protein expression according to claim 2, wherein the cis element with any number selected in a range of 1 to 10 is/are linked upstream of the promoter of the gene encoding the protein.

17. The expression vector according to claim 5, wherein the nucleic acid sequence for protein expression comprises a nucleic acid sequence for the artificial transcription factor to be expressed comprising: a gene encoding the artificial transcription factor; and a promoter for the gene encoding the artificial transcription factor, the promoter being linked upstream of the gene encoding the artificial transcription factor.

18. The expression vector according to claim 6, wherein in the nucleic acid sequence for protein expression, the cis element with any number selected in a range of 1 to 10 is/are linked upstream of the promoter of the gene encoding the protein.

19. The transformant according to claim 9, wherein the nucleic acid sequence for protein expression comprises a nucleic acid sequence for the artificial transcription factor to be expressed comprising: a gene encoding the artificial transcription factor; and a promoter for the gene encoding the artificial transcription factor, the promoter being linked upstream of the gene encoding the artificial transcription factor.

20. The transformant according to claim 10, wherein in the nucleic acid sequence for protein expression, the cis element with any number selected in a range of 1 to 10 is/are linked upstream of the promoter of the gene encoding the protein.

* * * * *